United States Patent
Pafford et al.

(10) Patent No.: US 8,702,760 B2
(45) Date of Patent: Apr. 22, 2014

(54) DYNAMIC SPINAL STABILIZATION SYSTEM

(75) Inventors: John Pafford, Eads, TN (US); Thomas G. Wilson, Guilford, CT (US)

(73) Assignee: Spine Wave, Inc., Shelton, CT (US)

( * ) Notice: Subject to any disclaimer, the term of this patent is extended or adjusted under 35 U.S.C. 154(b) by 1036 days.

(21) Appl. No.: 12/432,247

(22) Filed: Apr. 29, 2009

(65) Prior Publication Data

US 2009/0254123 A1 Oct. 8, 2009

Related U.S. Application Data

(62) Division of application No. 10/749,822, filed on Dec. 31, 2003, now abandoned.

(51) Int. Cl.
*A61B 17/70* (2006.01)

(52) U.S. Cl.
USPC .......................................... 606/265; 606/301

(58) Field of Classification Search
USPC ............... 606/264–278, 54–59, 300–331, 75
See application file for complete search history.

(56) References Cited

U.S. PATENT DOCUMENTS

| | | | | |
|---|---|---|---|---|
| 254,473 A * | 3/1882 | Gates | .......................... | 24/135 N |
| 1,796,409 A * | 3/1931 | Schuler | .......................... | 403/396 |
| 1,958,196 A * | 5/1934 | Lundy et al. | .................. | 439/811 |
| 2,102,896 A * | 12/1937 | Heinrich | ....................... | 439/779 |
| 2,210,750 A * | 8/1940 | Cook et al. | .................... | 174/94 S |
| 2,547,225 A * | 4/1951 | Mebold | ......................... | 403/396 |
| 3,997,138 A * | 12/1976 | Crock et al. | ................... | 248/67.5 |
| 4,041,939 A * | 8/1977 | Hall | ............................... | 606/254 |
| 4,078,559 A * | 3/1978 | Nissinen | ....................... | 606/258 |
| 4,569,338 A * | 2/1986 | Edwards | ....................... | 606/278 |
| 4,743,260 A * | 5/1988 | Burton | .......................... | 128/898 |
| 4,763,644 A * | 8/1988 | Webb | ............................. | 606/267 |
| 4,836,196 A * | 6/1989 | Park et al. | ..................... | 606/246 |
| 5,042,982 A * | 8/1991 | Harms et al. | ................... | 606/256 |
| 5,152,303 A * | 10/1992 | Allen | ............................ | 128/898 |
| 5,176,680 A * | 1/1993 | Vignaud et al. | ............... | 606/302 |
| 5,217,497 A * | 6/1993 | Mehdian | ....................... | 606/268 |
| 5,236,377 A * | 8/1993 | Goto | ............................. | 439/779 |
| 5,257,994 A * | 11/1993 | Lin | ............................... | 606/272 |
| 5,306,275 A * | 4/1994 | Bryan | ........................... | 606/914 |
| 5,312,402 A * | 5/1994 | Schlapfer et al. | ............... | 606/53 |
| 5,486,174 A * | 1/1996 | Fournet-Fayard et al. | ... | 606/261 |
| 5,501,684 A * | 3/1996 | Schlapfer et al. | ............. | 606/301 |
| 5,549,608 A * | 8/1996 | Errico et al. | ................... | 606/264 |
| 5,591,166 A * | 1/1997 | Bernhardt et al. | ............. | 606/266 |
| 5,672,176 A * | 9/1997 | Biedermann et al. | ......... | 606/271 |
| 5,810,819 A * | 9/1998 | Errico et al. | ................... | 606/266 |
| 5,938,663 A * | 8/1999 | Petreto | .......................... | 606/278 |
| 5,954,725 A * | 9/1999 | Sherman et al. | ................ | 606/78 |
| 5,964,760 A * | 10/1999 | Richelsoph | .................... | 606/279 |
| 5,989,250 A * | 11/1999 | Wagner et al. | ................. | 606/250 |
| 6,063,090 A * | 5/2000 | Schlapfer | ...................... | 606/270 |

(Continued)

*Primary Examiner* — Mary Hoffman
(74) *Attorney, Agent, or Firm* — Hoffmann & Baron, LLP

(57) ABSTRACT

A dynamic stabilization system includes a stabilization element, such as a spinal rod, a plurality of bone anchors, such as bone bolts, and a like plurality of connectors for connecting the bolts to the spinal rod. At least some of the connectors include a flexible element between the bone anchor and the rod and an adjustment element for adjusting the flexibility of the flexible element, to thereby adjust the dynamic flexibility between the rod and the bone anchor. In one embodiment, the flexible element is a flexible bearing element of a rod end bearing.

9 Claims, 2 Drawing Sheets

(56) References Cited

U.S. PATENT DOCUMENTS

| | | | |
|---|---|---|---|
| 6,077,262 A * | 6/2000 | Schlapfer et al. | 606/305 |
| 6,309,390 B1 * | 10/2001 | Le Couedic et al. | 606/264 |
| 6,315,779 B1 * | 11/2001 | Morrison et al. | 606/281 |
| 6,355,039 B1 * | 3/2002 | Troussel et al. | 606/264 |
| 6,371,957 B1 * | 4/2002 | Amrein et al. | 606/272 |
| 6,620,164 B2 * | 9/2003 | Ueyama et al. | 606/261 |
| 6,626,904 B1 * | 9/2003 | Jammet et al. | 606/266 |
| 6,796,003 B1 * | 9/2004 | Marvel | 24/135 N |
| 6,911,030 B1 * | 6/2005 | Vanacker et al. | 606/270 |
| 2001/0047173 A1 * | 11/2001 | Schlapfer et al. | 606/72 |
| 2005/0080419 A1 * | 4/2005 | Donath | 606/61 |
| 2005/0113833 A1 * | 5/2005 | Davison | 606/61 |

* cited by examiner

DYNAMIC SPINAL STABILIZATION SYSTEM

CROSS REFERENCE TO RELATED APPLICATION

The present application is a divisional application of and claims priority to application Ser. No. 10/749,822, filed on Dec. 31, 2003, now abandoned in the name of the same inventors and entitled "Dynamic Spinal Stabilization System."

The present invention relates to spinal implant systems, and particularly to systems for stabilization of the spine. The invention provides a dynamic stabilization system that permits limited relative movement between the instrumented vertebrae and the stabilization system.

In the past, the principal protocol for the treatment of the spine has been rigid fixation combined with fusion of the affected vertebral body or intervertebral disc. Arthrodesis, as this approach is known, has been achieved with a variety of rigid fixation elements, such as spinal rods or plates that are rigidly fixed to a vertebra using bone screws, bone bolts and spinal hooks. However, spinal fusion has been recognized to have limitations in the treatment of disc degeneration, especially in the earlier stages of the degeneration where it may be unnecessary to eliminate motion of the spinal motion segments.

Clinical studies suggest that cells of the intervertebral disc respond favorably to reduced (but not eliminated) mechanical loading through deposition of extracellular matrix proteins (collagen, proteoglycan, fibronectin, etc.) into the disc space. In some cases, a degenerated disc may simply involve a mechanically overloaded and hypermobile segment that can be repaired by reversing the mechanically damaging load environment. For instance, clinical experiences with dynamic stabilization systems suggest that the disc becomes increasingly hydrated over time, as judged by MRI scanning.

Spinal instability is a recognized effect of degenerative disc disease. In contrast to arthrodesis, arthroplasty is a protocol that contemplates restoring segmental spinal motion while treating the degenerative condition. Arthroplasty has been successfully used in the treatment of degenerative conditions of the hip and knee. In recent years, efforts have been made to implement arthroplasty in the spine, and most particularly in the intervertebral space. Intradiscal arthroplasty is now clinically available in the form of articulating prosthetic discs and polymeric disc nucleus replacements. With the availability of viable intradiscal arthroplasty devices, interest has grown in providing some means for dynamic spinal stabilization—i.e., stabilization that still permits some degree of mobility between spinal segments.

Drawing from the approaches developed for intradiscal arthroplasty, efforts have made to develop an extradiscal arthroplasty. These systems offer the advantage of "soft stabilization" that limit, rather than eliminate, spinal segment motion. Current theories suggest that preventing movement of the spinal segments may not be a significant factor in clinical success of spinal stabilization systems. Instead, these theories focus on creating a normal loading pattern for the spine as a primary vehicle for successful spinal instrumentation. Thus, the goal for dynamic stabilization has been to restrict movement of the spine to a zone or range where normal or near normal loading of the spinal segments can occur. At the same time, dynamic stabilization techniques have sought to prevent the spine from adopting a position or orientation where abnormal loading of the spine can occur.

One approach to achieve these goals for dynamic stabilization utilizes the spinous process. Thus, in one system, flexible "ligaments" are engaged around the spinous process of adjacent vertebrae. Another form of flexible "ligament" is attached to the spinous process by way of small screws. In yet another approach, a polymeric spacer is held in place between the adjacent spinous processes. One system utilizes a coil spring that spans several vertebrae and that is anchored to the lamina of the end vertebrae. In one version, a rod extends through part of the coil spring to control rotation.

Some dynamic stabilization systems have relied upon fixation to the pedicle of the vertebrae. In these types of systems, a pedicle screw is threaded into the pedicle of adjacent vertebrae. A member spans between the heads of the pedicle screws to limit the movement of the spinal segments. In one device, known as the Graf Ligament, a non-elastic band is wrapped around pedicle screw anchors. The non-elastic bands lock the spinal segment into lordosis, while permitting minimal rotation movements of the spine.

Another system utilizing pedicle screws, provided by Sulzer Spine-Tech as the Dynesys System, incorporates a polymeric cylinder between the bone anchors. The Dynesys System permits, but limits, relative motion between adjacent vertebrae. The FASS System essentially integrates features from the Graf and Dynesys systems.

The DSS System employs still another approach by including a spring element connected to pedicle screws. The spring element is contained within a polyurethane tube to prevent tissue ingrowth. Finally, some systems utilize a rigid member, such as a spinal plate, spanning between vertebrae. The flexible stabilization feature is incorporated into the interface between the pedicle screw and the rigid member, such as through a flexible washer or a spherical screw-plate interface.

These prior extradiscal arthroplasty approaches all involve the introduction of flexible elements between spinal motion segments. Consequently, many of these systems are susceptible to over-loading the disc annulus or are, by necessity, unduly restrictive with respect to motion of the spinal segment.

Moreover, these prior systems are not capable of altering the stiffness of a segment in various loading modes (e.g., flexion/extension, compression, lateral bending and axial rotation). Furthermore, these early approaches to arthrodesis do not allow selection of where, or at which motion segment, dynamic movement is permitted. Finally, no system exists that can readily convert to and from a soft stabilization to a more rigid or completely rigid system.

SUMMARY OF THE INVENTION

In response to these limitations of the prior art, the present invention contemplates a dynamic stabilization system that relies upon flexible elements interposed between a bone anchor, such as a bone screw or spinal hook. and a stabilization member, such as a rod or a plate. Furthermore, the present invention incorporates features that allow "fine tuning" of the dynamic flexibility of the total construct during the initial spinal instrumentation surgery, and even later during a revision procedure.

In one embodiment of the invention, a dynamic stabilization system for stabilization of the spine comprises a stabilization element configured to span between at least two vertebrae of the spine, at least two bone anchors, each having a bone engagement portion, and at least two connectors for connecting a corresponding one of the bone anchors to the stabilization element. At least one of the connectors includes a flexible element between the bone anchor and the stabilization element to permit relative pivoting therebetween. In another embodiment, the connector also includes an adjustment element for adjusting the flexibility of the flexible element.

In certain embodiments, the connector includes a bearing member attached to the stabilization element, in which the bearing member includes the flexible element. Where the stabilization element includes an elongated spinal rod, the bearing member is a rod end bearing including a rod engagement portion, and the flexible element is a bearing element of the rod end bearing. Where an adjustment element is provided, the bearing element is received within a bearing race of the rod end bearing and the adjustment element is arranged to compress the bearing element within the bearing race. The rod engagement portion includes a bore for receiving a portion of the spinal rod therein and a set screw for clamping the spinal rod within the bore.

In another embodiment of the invention, at least one of the bone anchors of the stabilization system includes a stem having a threaded portion and the flexible element includes a bore for receiving the stem therethrough. In certain embodiments, the adjustment element includes a nut engaging the threaded portion and arranged to compress the flexible element as the nut is threaded onto the threaded portion.

The dynamic stabilization system of the present invention can include come connectors that are configured to substantially rigidly connect one of the bone anchors to the stabilization element. Thus, the stabilization system can include a mix of rigid and flexible connectors that integrate the bone anchors to the stabilization element spanning the spine.

In embodiments of the dynamic stabilization system in which the stabilization element is an elongated spinal rod, at least one of the bone anchors includes a stem having a threaded portion and defining slot sized to receive the spinal rod therethrough. The flexible element includes a sleeve disposed around the stem with at least a portion disposed between the bone engagement portion of the bone anchor and the spinal rod when the rod extends through the opening. Where an adjustment element is provided, it includes a nut engaging the threaded portion that is arranged to compress the sleeve as the nut is threaded onto the threaded portion. In certain embodiments, the flexible element includes a first sleeve disposed between the bone engagement portion and the spinal rod and a second sleeve disposed between the spinal rod and the nut. In other embodiments, the sleeve is disposed between the bone engagement portion and the nut and includes an opening for receiving rod therethrough when the rod extends through the slot in the stem.

In embodiments of the dynamic stabilization system in which the stabilization element is an elongated spinal plate defining at least one opening therethrough, at least one of the bone anchors includes a stem having a threaded portion and the flexible element is a bushing engaged within the opening. The bushing defines a bore for receiving the stem therethrough and includes an upper head portion disposed between spinal plate and the nut. An adjustment element includes a nut engaging the threaded portion, whereby the nut compresses the head portion when the nut is threaded onto the threaded portion. In certain embodiments, the flexible element includes a lower head portion disposed between the spinal plate and the bone engaging portion of the bone anchor. The bone anchor further includes an intermediate portion between the bone engagement portion and the lower head portion of the bushing.

The present invention contemplates a method for dynamic stabilization of motion segments of the spine comprising the steps of positioning a stabilization element adjacent the spine, the stabilization element configured to span a length of the spine between at least two motion segments, engaging bone anchors to at least two motion segments, and coupling the bone anchors to the stabilization element with a flexible element between at least one bone anchor and the stabilization element. The method further contemplates the step of adjusting the flexibility of the flexible element. This step of adjusting the flexibility includes compressing the flexible element. This method can be coupled with the step of repairing or replacing all or part of the intervertebral disc between at least two motion segments. In a more specific embodiment, the method is coupled with the replacement or augmentation of all or part of the nucleus pulposus with a polymeric prosthesis adapted to emulate the physical properties of the natural nucleus.

In another aspect of the invention, a method for dynamic stabilization of a motion segment of the spine comprises the steps of introducing a device into an intervertebral space to at least partially maintain or restore the natural motion of the disc at the motion segment and then coupling a dynamic stabilization system across the motion segment that permits natural motion of the disc. The device can include a device for replacing or augmenting the nucleus pulposus of the intervertebral disc. In certain embodiments, the device includes a polymeric prosthesis configured to replace or augment the nucleus pulposus in which the polymeric prosthesis exhibits physical properties similar to the natural nucleus pulposus.

It is one object to provide a system for the dynamic stabilization of the spine in which at least some of the natural motion of a spinal motion segment is retained. It is another object to provide a dynamic stabilization system that permits adjustment in the flexibility at different locations along the dynamic construct.

One benefit of the present invention is that it can be readily adapted to existing stabilization constructs and can be integrated with known constructs that are fixed or that permit limited micro-motion. Another benefit is that the invention provides the orthopaedic surgeon with a great deal of flexibility in the initial surgical procedure or in a subsequent revision procedure.

Other objects and benefits of the invention can be discerned from the following written description taken along with the accompanying figures.

DESCRIPTION OF THE PREFERRED EMBODIMENTS

Figure 1:
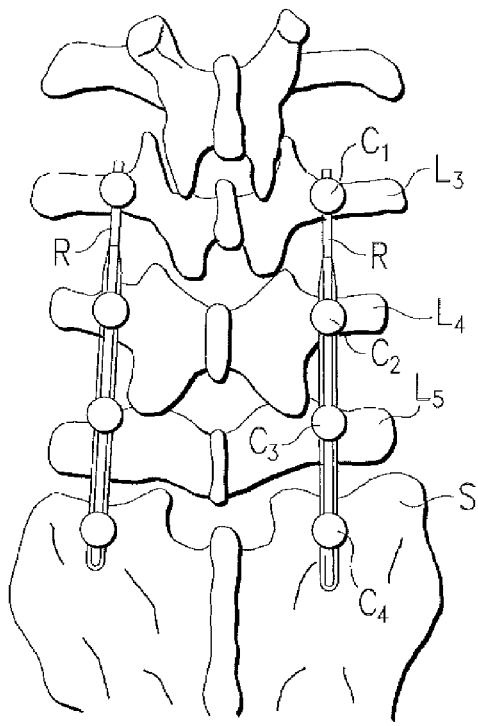
FIG. 1 is an anterior view of a human spine instrumented with a stabilization construct.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

An exemplary spinal construct is depicted in FIG. 1. In this construct, a scaffolding is affixed to opposite sides of the spine. In the illustrated configuration, a pair of stabilization elements, in the form of spinal rods R, span from the L3 vertebra, across the L4 and L5 vertebrae and ending at the sacrum S. A series of connectors C1-C4 fasten the rod R to the vertebrae. The connectors in a typical stabilization construct include some form of anchor element, such as a bone screw or a spinal hook. In recent years, the pedicle screw has become a bone anchor of choice.

In prior stabilization constructs, the connectors and associated bone anchors have been common at each instrumented vertebral level. In the typical case, the stabilization element, such as rod R, was rigidly fixed to the bone anchor, or at best was permitted some "micro-motion". In accordance with one feature of the present invention, the connectors C1-C4 can be different—e.g., they can provide different levels of flexibility or rigidity depending upon the physiological requirements for the particular patient and the nature of the injury or damage to the spine that is being addressed by the stabilization construct.

Connectors and bone anchors for a generally rigid fixation are well known. Connectors providing dynamic stabilization may be constructed in accordance with the embodiments disclosed herein. For instance, in one embodiment, a connector 10, depicted in FIG. 2, includes a bone anchor 12 that is in the form of a bone screw with bone engaging threads 13. The bone anchor 12 includes an intermediate platform 15 from which projects a post 16. The post 16 includes a non-threaded portion 17 and terminates in a threaded portion 18. The threaded portion 18 preferably carries machine threads for engaging a threaded nut 20. As thus far described, the bone anchor is constructed similar to the bone screw described and illustrated in U.S. Pat. No. 4,836,196 to Park et al., the disclosure of which is incorporated herein by reference. It is understood that the post 16 can include an internal or an external driving feature (not shown) for engagement by a tool to thread the bone threads 13 into a vertebra. It is also contemplated that a locking nut is provided that can lock the position of nut 20 on the bone anchor 12.

Figure 2:
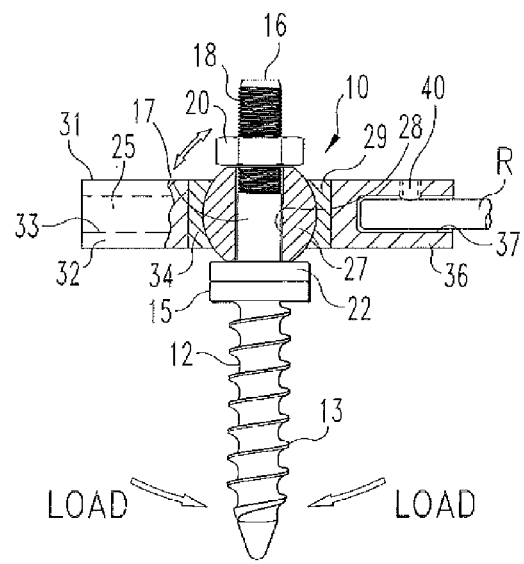
FIG. 2 is a side view of a connector capable of providing dynamic fixation within the stabilization construct shown in FIG. 1.

The bone anchor 12 is engaged to the stabilization element R by way of a bearing member 25. The bearing member is similar to a rod-end bearing used in industrial machinery applications. For example, the bearing member 25 can be similar to the HME self-lubricating rod end manufactured by Heim Bearings of Fairfield, Conn. The bearing member 25 includes a bearing element 27 that defines a passageway 28 to receive the stem 16 of the bone anchor 12, as shown in FIG. 2. The bearing element is slidably disposed within a bearing race 29 so that the bearing element 27 articulates within the race in its permitted degrees of freedom.

Figure 3:
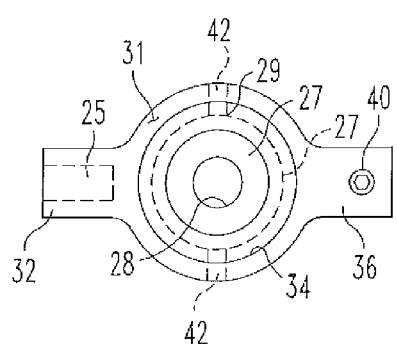
FIG. 3 is a top view of a flexible bearing component of the connector illustrated in FIG. 2.

The race 29 is mounted within a bore 34 defined in a bearing housing 31. The race is fixed within the housing in a conventional manner, such as by a press-fit engagement. As shown in FIGS. 2-3, the housing 31 generally conforms to the shape of the bearing element 27—in this case the bearing element is spherical so the housing is circular. The housing defines at least one rod engagement element 32. When the connector 10 is situated at the end of a construct, such as the connector C1 in FIG. 1, only one engagement element is necessary. However, if the connector 10 is situated within the length of the construct, such as the connectors C2 or C3, then a second rod engagement element 36 can be provided on the housing 31.

The rod engagement element 32 is configured for attachment or connection to the stabilization rod R. Thus, in its simplest form, the element 32 is welded to the rod end. Preferably, the engagement element 32 defines a bore 33 for snugly receiving the rod end. Alternatively, the element 32 can define a press-fit engagement with the rod end. The bore 33 and the rod end can define complementary non-circular features to prevent rotation of the rod about its axis within the rod engagement element 32.

Most preferably, some additional fixation is provided to positively and solidly engage the bearing housing to the rod R. Thus, as shown with respect to the rod engagement element 36, the rod bore 37 is intersected by a set screw 40, which is configured as is typical for spinal implants. The set screw can be threaded into the engagement element 37 to bear against the rod end to clamp the bearing housing 31 to the rod R. Several set screws 40 are provided to ensure a solid fixation between the two parts.

As shown in FIG. 2, the stem 16 of the bone anchor 12 extends through the bore 28 in the bearing element 27. The bearing element is sandwiched between the intermediate portion 15 of the bone anchor and the nut 20. Alternatively, a spacer 22 may be interposed between the intermediate portion 15 and the bearing element 27. The spacer 22 can be utilized where necessary to accommodate height differences between the rod and the vertebrae along the length of the rod R.

In accordance with the present invention, the bearing member 25 allows articulation of the rod R and bone anchor 12 relative to each other in certain degrees of freedom. For instance, the stem 16 of the bone anchor can move in the direction of the arrows in FIG. 2 when subjected to the loads applied to the threaded portion 13 of the anchor that is engaged within a vertebra. The present invention contemplates a connector 10 that allows adjustment of the relative flexibility of this articulating bearing joint. Thus, in one specific embodiment, at least one set screw 42 is threaded into the housing 31 to engage the bearing element 29, as shown in FIG. 3. In this specific embodiment, the bearing element 29 is fixed to the housing 31, thereby producing an essentially rigid connection between the bone anchor 12 and the stabilization rod R.

In another embodiment, the degree of flexibility is adjusted by the amount of compression of the bearing element 27. In this embodiment, the bearing element is formed of an elastomeric material that is compressed between the intermediate portion 15 and the nut 20. As the nut is tightened onto the threaded end 18 of the stem 16, it presses the bearing element 27 which causes it to bulge transverse to the compressive force. As the bearing element bulges, it presses outward into the race 29, thereby increasing the frictional resistance between the two components. Thus, the nut 20 operates as an adjustment element to adjust the dynamic flexibility of the bearing element.

It can be appreciated that this flexibility adjustment can occur at any time during the life of the stabilization construct. In other words, the construct can be initially implanted with a particular degree of flexibility in the connector 10 at any instrumented vertebral level. Moreover, if it is later determined that this degree of flexibility requires adjustment, minimally invasive procedures can be used to access the nut 20 and either tighten or loosen the nut depending upon whether the connector 10 needs less or more flexibility.

It is understood that the elements of the connector must be formed of medical grade materials, and especially of materials that can withstand the extreme loads experienced by the spinal construct. Thus, the bone anchor 12, nut 20 and bearing housing 31 may be formed of a biocompatible metal, such as stainless steel or titanium. The bearing race 29 can also be formed of a biocompatible metal, provided that its surface is polished to provide a sufficient articulating surface for the bearing element. Preferably, the bearing race 29 is formed of a biocompatible polymer, including UHMWPE, PTFE, nylon, polyurethane, or thermoplastic elastomers, such as HYTRL™. The bearing element 27 may be formed of the same material as the bearing race. Alternatively, the bearing element may be formed of a material that is more elastic than the material of the bearing race.

In the embodiment illustrated in FIG. 2, the bearing element 27 is spherical and the race 29 defines an articulating surface. Thus, with this embodiment, the connector nominally permits relative movement between the rod R and the bone anchor 12 (and consequently the instrumented vertebra) in several degrees of freedom and in several planes that intersect the plane of the rod and bone anchor. Thus, while the pivot arrows in FIG. 2 reside in the rod/bone anchor plane, the bone anchor can also pivot along transverse planes projecting out of the paper. In many stabilization constructs, the dynamic stabilization is limited to specific planes or degrees of freedom, and most particularly to the rod/bone anchor plane (i.e., the plane of the paper in FIG. 2).

Figure 4:
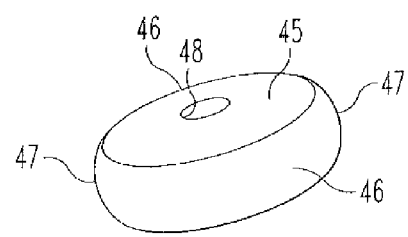
FIG. 4 is a perspective view of an alternative bearing element for use in a flexible bearing component of the type depicted in FIG. 3.

In order to control the degree of freedom of the connector 10, the set screws 42 can be replaced with pivot pins that fit within corresponding bores (not shown) formed in the bearing element 27. Alternatively, the bearing element can assume different configurations, such as the oblong element 45 shown in FIG. 4. The element 45 defines a central bore 48 for receiving the stem 16 of the bone anchor 12. This oblong bearing element includes generally linear sides 46 bounded by generally spherically shaped ends 47. The bearing race can be configured accordingly to receive the oblong bearing element 45. The generally linear sides 46 prevent pivoting relative to those surfaces, while the spherical ends 47 permit pivoting in that corresponding plane. The bearing element 45 exhibits the same compressive properties as the element 27 discussed above to permit adjustment of the flexibility of the bearing joint.

In one feature of the invention, the interface between the bone anchor and the stabilization element is adjustable, either during or subsequent to the initial surgery in which the stabilization scaffolding is implanted. This feature is accomplished by the use of elastomeric elements that can be compressed to adjust their dynamic flexibility. This feature is implemented in an additional embodiment of the present invention depicted in FIGS. 5 and 6. In this embodiment, a connector 50 includes a bone anchor 52 that includes bone engaging threads 53, an intermediate portion 55 and a stem 56 having a non-threaded portion 57 and a threaded end 59. A nut 60 is also provided for engaging the threaded end of the stem. The bone anchor 52 is thus far similar to the anchor 12 described above.

However, with this embodiment, the non-threaded portion 57 of the stem 56 defines a vertical slot 58 configured to receive the stabilization rod R therethrough. Preferably, the width of the slot is close to the outer diameter of the rod, while the vertical height of the slot is greater than the diameter. As can be seen in the figures, the rod R passes through the vertical slot 58 and is sandwiched between opposite sleeves $65_U$ and $65_L$. Both sleeves are preferably formed of an elastomeric material that is resiliently compressed as the bone anchor 52 pivots in the direction indicated by the arrows in FIG. 5. The sleeves $65_U$ and $65_L$ define a bore 66 through which the stem 56 of the bone anchor 52 extends.

As with the previous embodiment, the nut 60 is used to change the dynamic flexibility of the connector 50 by adjusting the amount that the resilient sleeves $65_U$ and $65_L$ are compressed. A washer (not shown) is provided between the nut 60 and the uppermost sleeve $65_U$ so that tightening the nut does not compromise the integrity of the sleeve. The dynamic flexibility of the connector 50 may also be adjusted by using sleeves having different thicknesses or different elastomeric material properties. The elongated slot 58 may be sized to accommodate an expected range of thicknesses of the lowermost sleeve $65_L$.

Figure 5:
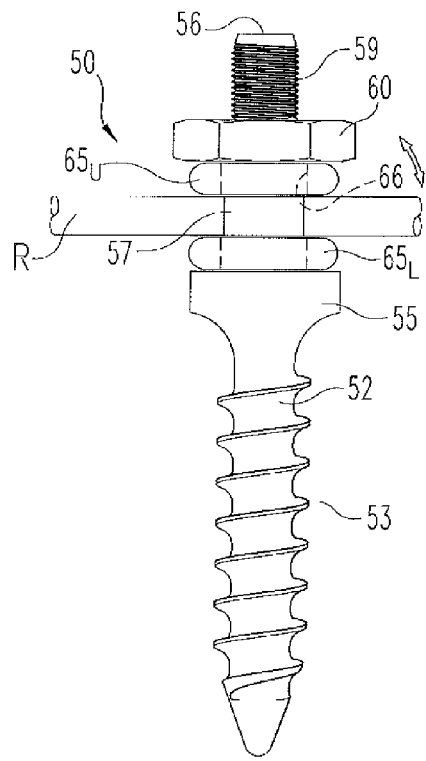
FIG. 5 is a side view of a connector according to a further embodiment of the invention for providing dynamic fixation within the stabilization construct shown in FIG. 1.
Figure 6:
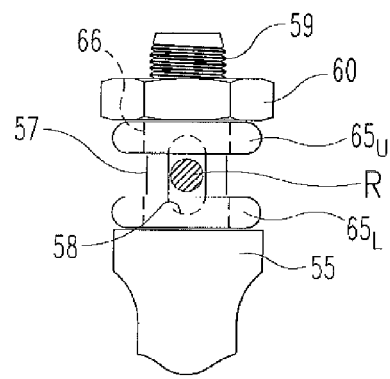
FIG. 6 is a side partial view of the connector shown in FIG. 5.
Figure 7:
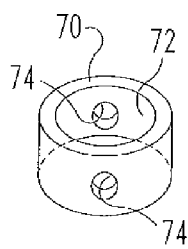
FIG. 7 is a perspective view of an elastomeric sleeve for use with the connector 50 shown in FIG. 5.

In the embodiment shown in FIGS. 5 and 6, upper and lower sleeves $65_U$, $65_L$ are provided. In an alternative embodiment, a single sleeve 70 may be utilized, as shown in FIG. 7. The sleeve defines a bore 72 that is sized to receive the stem 56 of the bone anchor 52. The sleeve 70 further defines a transverse bore 74 that is sized to receive the stabilization rod R. The sleeve 70 can be compressed by the nut 60 to adjust the dynamic flexibility of the connector, in the manner described above.

Figure 9:
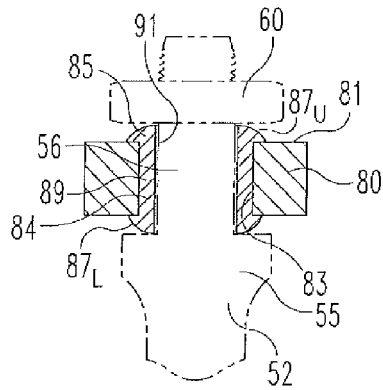
FIG. 9 is a cross-sectional view of the stabilization plate shown in FIG. 8, taken along line 9-9 as viewed in the direction of the arrows.
Figure 8:
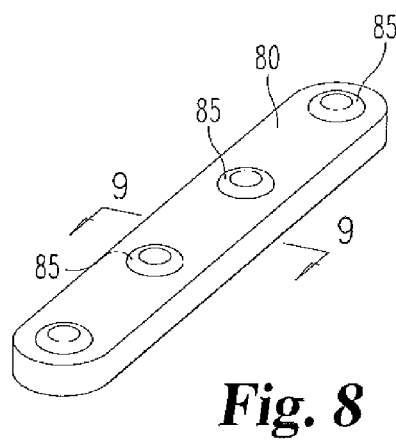
FIG. 8 is a perspective view of a stabilization plate for use in a dynamic spinal stabilization construct.

Adjustability of dynamic flexibility of a stabilization construct may also be implemented in a system that relies upon an elongated stabilization plate. In particular, a stabilization plate 80, as shown in FIGS. 8-9, is provided with a plurality of openings 83 for engagement with a plurality of bone anchors, such as the anchor 52 depicted in phantom lines in FIG. 9. The stabilization plate is sized to span several vertebral levels, with the openings 83 spaced accordingly. The openings in the plate 80 may be individual bores or may be in the form of elongated slots, similar to the slotted spinal plate disclosed in U.S. Pat. No. 4,836,196, the disclosure of which has been incorporated by reference.

In order to provide the dynamic flexibility feature of the present invention, the plate 80 includes a plurality of elastomeric bushings 85 that are pressed into a corresponding one of the openings 83. As shown in FIG. 9, the bushings 85 include a central collar 84 that is sized to fit within an opening 83, preferably snugly. The collar defines a bore 91 for receiving the stem 56 of the anchor 52 therethrough and an outer surface 89 that may contact the corresponding opening 83 of the plate. The collar terminates at its ends in upper and lower head portions $87_U$, $87_L$ that are larger than the openings 83 in the plate 80 to trap the bushing 85 within the opening. The head portions $87_U$ and $87_L$ may bear directly against the outer surface 81 of the plate 80.

The lower head portion $87_L$ is supported on the intermediate portion 55 of the anchor, which the nut 60 bears against the upper head portion $87_U$. The two head portions $87_L$ and $87_U$ are compressed by tightening the nut 60 onto the stem 56 of the bone anchor 52, to thereby increase the rigidity (or decrease the dynamic flexibility) of the plate-to-bone anchor interface.

The dynamic stabilization system of the present invention is well suited as an adjunct to a disc repair procedure. For instance, an intervertebral disc may require augmentation or replacement, depending upon the severity of the damage or disease to the disc. Where the disc is intact, it is important to maintain the loading pattern as normal as possible since this loading pattern helps hydrate the disc and flush toxins from the disc. The dynamic stabilization systems disclosed herein provide stabilization for the affected disc while allowing a meaningful amount of motion at that vertebral level.

Devices have been developed for replacement of the intervertebral disc. In some cases, the device is a mechanical device that is configured to mimic the mechanics of the disc motion. In more recent years, the nucleus pulposus of the intervertebral disc has been replaced with a polymer prosthesis that emulates the physical and chemical properties of the disc. In particular, these types of prostheses are intended to preserve or restore the movement and load response of the affected disc as close to the natural disc as possible. One such material is a hydrogel that has similar elastic properties to the natural nucleus pulposus and that shares a similar fluid transport mechanism to the natural disc. This material can be used to replace the entire nucleus pulposus, or to augment the existing nucleus where voids or other defects in the nucleus exist.

Even where the intervertebral disc has been replaced with a mechanical device, or where all or part of the nucleus pulposus has been replaced or augmented by a polymer prosthesis, restoration and maintenance of normal spinal segment motion is important. Consequently, it is contemplated that the dynamic stabilization system of the present invention, including connectors 10, 50 or the plate 80, may be used in connection with disc/nucleus repair or replacement procedures.

Thus, in one aspect of the invention, a method for dynamic stabilization of a motion segment includes the step of introducing a device into an intervertebral space that at least partially restore or maintain the natural motion of the intervertebral disc. The motion segment is instrumented with a dynamic stabilization system that includes one or more of the connectors 10, 50 or the plate 80, which permits the natural motion of the disc.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A dynamic stabilization system for stabilization of the spine, comprising:
   an elongated spinal rod configured to span between at least two vertebrae of the spine:
   at least two bone anchors, each having a bone engagement portion, at least one of said bone anchors includes a stem having a threaded portion and defining a slot sized to receive said spinal rod therethrough; and
   at least two connectors for connecting a corresponding one of said bone anchors to said spinal rod, at least one connector configured to substantially non-rigidly connect one of said bone anchors to said spinal rod including;
      a flexible element between the bone engagement portion of the bone anchor and the spinal rod to permit relative pivoting therebetween, said flexible element including a sleeve encircling said stem with at least a portion disposed in engagement with the spinal rod when the encircling said stem the rod extends through said slot; and
      an adjustment element for adjusting the flexibility of said flexible element, said adjustment element including a nut engaging said threaded portion and arranged to compress said sleeve against said rod as said nut is threaded onto said threaded portion.

2. The dynamic stabilization system according to claim 1, wherein said at least one of said bone anchors includes an intermediate portion between said stem and said bone engagement portion, said intermediate portion configured to support said sleeve so that said sleeve is compressed between said intermediate portion and said nut when said nut is threaded onto said threaded portion.

3. The dynamic stabilization system according to claim 1, wherein another of said connectors is configured to substantially rigidly connect one of said bone anchors to said spinal rod.

4. The dynamic stabilization system according to claim 1, wherein said flexible element includes a first sleeve disposed between said bone engagement portion and the spinal rod and a second sleeve disposed between said spinal rod and said nut.

5. The dynamic stabilization system according to claim 1, wherein said sleeve is disposed between said bone engagement portion and said nut and includes an opening for receiving rod therethrough when said rod extends through said slot in said stem.

6. A dynamic stabilization system for stabilization of the spine, comprising:
   an elongated spinal stabilization rod configured to span between at least two vertebrae of the spine:
   at least two bone anchors, each having a bone engagement portion and at least one of said bone anchors including a stem defining slot sized to receive said spinal rod therethrough; and
   a flexible sleeve encircling said stem, said flexible sleeve being in engagement with said rod with at least a portion of said sleeve disposed between the bone engagement portion of the bone anchor and the spinal rod when the rod extends through said slot.

7. The dynamic stabilization system according to claim 6, wherein:
   said stem includes a threaded portion, and
   said system further comprises a nut engaging said threaded portion and arranged to compress said sleeve as said nut is threaded onto said threaded portion.

8. The dynamic stabilization system according to claim 7, wherein said flexible sleeve includes a first sleeve disposed between said bone engagement portion and the spinal rod and a second sleeve disposed between said spinal rod and said nut.

9. The dynamic stabilization system according to claim 8, wherein said flexible sleeve is disposed between said bone engagement portion and said nut and includes an opening for receiving rod therethrough when said rod extends through said slot in said stem.

* * * * *